United States Patent [19]

Sing

[11] Patent Number: 5,133,978

[45] Date of Patent: Jul. 28, 1992

[54] HIGH VISCOSITY BACTERIAL COMPOSITIONS AND METHODS

[76] Inventor: Wesley D. Sing, 8216 E. Walnut Way, Indianapolis, Ind. 46256

[21] Appl. No.: 562,739

[22] Filed: Aug. 3, 1990

[51] Int. Cl.$^5$ ................................................ A23C 9/12
[52] U.S. Cl. ...................................... 426/36; 426/34; 426/38; 426/42; 426/43
[58] Field of Search ...................... 426/34, 36, 38, 42, 426/43

[56] References Cited

U.S. PATENT DOCUMENTS

| | | | |
|---|---|---|---|
| 3,968,256 | 7/1976 | Sing | 426/38 |
| 4,172,899 | 10/1979 | Vedamuthu | 426/38 |
| 4,318,928 | 3/1982 | Sing | 426/38 |
| 4,477,471 | 10/1984 | Gonzalez | 426/38 |
| 4,599,313 | 7/1986 | Gonzalez | 426/38 |

*Primary Examiner*—Joseph Golian
*Assistant Examiner*—Leslie Wong
*Attorney, Agent, or Firm*—Woodard, Emhardt, Naughton Moriarty & McNett

[57] ABSTRACT

Described are novel donor bacteria harboring a plasmid DNA fragment from a plasmid 30 MDa in molecular weight referred to as pHV67 in *L. lactis* subsp. *lactis* TC67, and DNA fragment encoding for a substance which increases viscosity of a milk-containing product. The donor bacteria are capable of conjugally transferring the DNA fragment to a lactic acid bacterium at a frequency of at least about $10^{-5}$ transconjugants per input donor bacterium. Methods involving the preparation and use of bacteria for novel milk fermentations, for example, buttermilk, sour cream and cottage cheese, are also described.

35 Claims, No Drawings

HIGH VISCOSITY BACTERIAL COMPOSITIONS AND METHODS

BACKGROUND

This invention relates generally to bacteria used in the fermentation of milk-containing products. More particularly, it relates to novel bacteria and bacterial compositions and methods which can be used to impart very high viscosity to fermented milk products.

By way of further background, for many years, fermented or "cultured" milk products have formed a substantial component of the human diet. For example, many cultured milk products have long been popular in North America, including for example buttermilk, sour cream, cottage cheese, dressings, pudding, yogurt and many others. Additional cultured milk products have long been popular in other areas. For example, while not well known in North America, sour milk products such as taette and long milk are popular in Sweden, and a firm, viscous cultured product known as "viili" is produced in notable quantities in Finland.

Producing these and other cultured dairy products depends on fermentation by lactic acid bacteria. As cultures of these bacteria grow in the milk product, they can impart certain characteristics such as acidity, flavor, and texture. Commonly used lactic bacteria for these purposes include strains from the genus Lactococcus, Lactobacillus, Streptococcus, Pediococcus and Leuconostoc. As will be appreciated, successful growth of these bacteria, and thus the successful production of quality endproduct, is a delicate process which can be affected by many physical and biological factors.

For instance, lactic acid bacteria are attacked by bacteriophage, which can lead to partial or complete loss of fermentations. See, for instance, Saxelin et al., "Ultrastructure and Host Specificity of Bacteriophages of *Streptococcus cremoris, Streptococcus lactis* subsp. *diacetylactis*, and *Leuconostoc cremoris* from Finnish Fermented Milk 'Viili'", *Applied and Environmental Microbiology*, October, 1986, pp. 771-777; and, U.S. Pat. No. 4,883,756 to Klaenhammer et al. Additionally, many of the desired phenotypes are encoded on extrachromosomal DNA, e.g. plasmid DNA, which results in frequent loss of desired phenotypes in culture transfers and other manipulations. Further, even assuming complete failure of fermentation can be avoided, it is often difficult to control the level of expression of a flavor, acidity, texture, etc. phenotype in a milk product, even though achieving this control can be crucial to success of endproduct. One method which has been used to control levels of expression is to combine the flavor, texture, or acid-producing bacteria with other bacteria which do not have the phenotype of interest. In this manner, the growth of the phenotypic bacteria can be inhibited by competition from the other bacteria. However, in many cases the differing types of bacteria included do not reproduce at the same rate and/or having differing phage sensitivities, and the ratio of the two types of bacteria, and thus the level of expression of the phenotype of interest, is not reliably controlled during culturing of the product.

As an example of one phenotype, the development of viscosity in cultured milk products has been of notable interest in the dairy industry. This viscosity is developed by growth of "viscous" (also commonly referred to as "slime-producing", "ropy" or "mucoid") strains of lactic bacteria. Viscous bacteria, like those responsible for other desired phenotypes, are subject to these same concerns of phage sensitivity, loss of phenotype, and control of expression in products. For example, there presently exist two primary approaches to producing viscous dairy products. One uses a viscous *L. cremoris* and a non-viscous lactococcal strain combined in the same culture. A second approach uses separate cultures, one containing viscous *L. cremoris* strains and another containing non-viscous lactococcal strains. Currently, both approaches fail to meet commercial demands for very high viscosity milk fermentations which must endure severe agitation during processing, maintain a minimal viscosity over long periods of storage, or meet higher viscosity criteria for cultured milk products or dairy based food additives.

In fermentations inoculated with a single culture containing both viscous and non-viscous lactococci, practical limits exist in the degree of viscosity that can be achieved. These limitations are a result of using lactococcal strains which inherently grow relatively slowly (*L. cremoris*) and/or carry plasmids which produce limited amounts of viscosity per cell. In this approach, the proportion of viscous strains must be restricted to a level where undesirable organoleptic properties are prevented. To increase endproduct viscosity, a culture manufacturer could attempt to create a culture with a higher proportion of viscous strains. However, such high proportions of viscous strains would offset the balance with non-viscous strains (strain domination), and possibly result in decreased fermentation due to bacteriophage attack. Attempts to leave cultures unchanged but alter the process to increase or maintain product viscosity have met with resistance from the industry in favor of conserving standard operating procedures and product formulations. Therefore, it has become imperative to develop new bacteria and methods which improve upon present industry standards, to meet the demand for reliable, controllable fermentations.

In general, the majority of lactic bacteria known to produce high viscosity are *Lactococcus cremoris* (previously *Streptococcus cremoris*) strains. These strains have been most often used in the production of the thick, doughy Swedish and Finnish sour milk products such as taette, long milk and viili. These viscous strains have not enjoyed widespread use in the dairy industry because it is difficult to reliably control the level of the viscous expression, and because they are particularly sensitive to loss of the viscous phenotype. See, D. Macura and P. M. Townsley, "Scandinavian Ropy Milk—Identification and Characterization of Endogenous Ropy Lactic Streptococci and Their Extracellular Excretion", *J. Dairy Sci.* 67: 735-744 (1984). Further, these viscous *L. cremoris* strains typically provide optimum viscosity when grown at a temperature of about 21° C., whereas producers of numerous of the known cultured milk products have optimized fermentation temperatures at about 23° to 25° C. Moreover, *L. cremoris* strains have also have been noted for their phage sensitivity.

Recognizing the value of the viscous phenotype but at the same time the limitations of the *L. cremoris* strains having it, investigators have attempted to discern where the viscous phenotype is encoded in various *L. cremoris* strains, and to develop methods to impart this quality to other types of bacteria having more desirable and varied biological properties. In so doing, the commercial impact of the research is limited by certain standards in the dairy industry. As an example, while natural (i.e. conjugal) transfer of genetic information is acceptable for constructing new strains for food production in the U.S., other non-natural types of transfer, such as transformation, are not. In the face of these and other technical and commercial constraints, the efforts to expand the number of available viscous strains to satisfy the need for improved fermentation systems have met with limited success.

In this vein, during the mid 1980's, E. R. Vedamuthu and J. M. Neville demonstrated that the ability to produce mucoidness (Muc+) in milk cultures in strain *Streptococcus cremoris* MS is encoded on an 18.5M dalton plasmid which was designated as pSRQ2202. "Involvement of a Plasmid in Production of Ropiness (Mucoidness) in Milk Cultures by *Streptococcus cremoris* MS", *Applied and Environmental Microbiology*, April 1986, pp. 677–682. The authors reported successfully achieving conjugal transfer of pSRQ2202 from *S. cremoris* MS to a nonmucoid *S. lactis* recipient ML-3/2.201, and subsequent transfer of pSRQ2202 from the resultant *S. lactis* mucoid strain to malty *S. lactis* 4/4.2 and to *S. lactis* subsp. *diacetylactis* SLA3.25. While the accepted mode of conjugal transfer was achieved in this work, the applicant, through independent study, has determined that pSRQ2202 confers only moderate viscosity and thus leaves much room for improvement.

Report of this work by Vedamuthu and Neville was soon followed by that of A. von Wright and A. Tynkkynen, "Construction of *Streptococcus lactis* subsp. *lactis* Strains with a Single Plasmid Associated with Mucoid Phenotype", *Applied and Environmental Microbiology*, June 1987, pp. 1385–1386. Von Wright and Tynkkynen reported obtaining lactose-metabolizing mucoid (Lac+⁻Muc+) variants of plasmid-free *Streptococcus lactis* subsp. *lactis* MG1614 by protoplast transformation with total plasmid DNA from Muc+ *S. lactis* subsp. *cremoris* ARH87. The authors concluded that the Muc+ function is encoded in a plasmid designated pVS5 from Muc+ *S. lactis* subsp. *cremoris* ARH87. Based on a restriction pattern obtained with restriction endonuclease BglII, the authors calculated the size of pVS5 to be 30 MDa, clearly larger than that of pSRQ2202 (18.5 MDa) reported by Vedamuthu and Neville in their work. Unfortunately, the type of genetic transfer (i.e. transformation) achieved by von Wright et al. is generally not acceptable to U.S. and other food producers, and thus their work is of limited commercial interest. Furthermore, these authors failed to demonstrate production of a high frequency conjugal donor of the viscous phenotype, which is essential to the development of successful commercial dairy ventures.

In 1988, work to expand the available viscous strains continued and another study of several ropy Swedish and Finnish *S. cremoris* strains was published. H. Neve et al., "Plasmid-encoded functions of ropy lactic acid streptococcal strains from Scandinavian fermented milk", *Biochimie* (1988) 70: 437–442. Neve et al. reported strong indications that the Rop+ phenotype in the Swedish strains was encoded on a 17 MDa plasmid and in the Finnish strains on a 30 MDa plasmid. Through a series of mating experiments, Neve et al. attempted to obtain conjugal transfer of these 17 and 30 MDa plasmids to *S. lactis* subsp. *diacetylactis* Bu2-59 (Rop⁻ Lac⁻). However, the authors reported that no transfer of the Rop+ phenotype could be observed from any of the mating experiments in their investigation.

In light of the foregoing discussion, it is evident that there are continuing needs for improvement in the field of cultured milk products. The number of available viscous strains remains limited despite efforts to expand it. The viscous *L. cremoris* strains have not achieved widespread use due to undesirable traits they exhibit. Attempts to transfer their viscous phenotype to other types of bacteria have met with only limited success. While successful conjugal transfer of the 18.5 MDa plasmid pSRQ2202 to a *L. lactis* strain has been achieved, this plasmid encodes for only moderate viscosity, and to applicant's knowledge no interspecies conjugal transfer of any other viscous plasmid from a *L. cremoris* strain has been reported. In fact, Neville et al. attempted just that but were unsuccessful. The work of von Wright et al. in which a viscous plasmid was transformed from a *L. lactis* subsp. *cremoris* to a *L. lactis* subsp. *lactis* is of general scientific interest; however, this mode of genetic transfer is not considered proper for food products in the U.S., Europe and possibly other countries. Further, von Wright et al. did not demonstrate obtaining a high frequency conjugal donor of a high viscous phenotype. Such a donor is essential in achieving food grade strategies for strain development necessary for significant commercial applications. It is in light of this extensive background that the applicants entered their study, and have now succeeded in developing novel bacteria, bacterial compositions, and methods to address these and other needs in the industry.

SUMMARY OF THE INVENTION

In addressing these needs, the invention provides in a first preferred embodiment a novel donor bacterium harboring a first DNA fragment from a plasmid 30 MDa in molecular weight referred to as pHV67 in *L. lactis* subsp. *lactis* TC67, the DNA fragment encoding for a substance which increases viscosity of a milk-containing product. This donor bacterium is able to conjugally transfer the DNA fragment to a lactic bacterium at a frequency of at least about $10^{-5}$ transconjugants per input donor bacterium. The donor bacterium provides for the first time a donor from which several very high viscosity lactic acid bacterial strains can be conjugally developed.

Another preferred embodiment of the invention relates to a method for producing a bacterium harboring a first DNA segment from a plasmid 30 MDa in molecular weight referred to as pHV67 in *L. lactis* subsp. *lactis* TC67, the DNA fragment encoding for a substance which increases viscosity of a milk-containing product. This method includes the step of conjugally mating a suitable recipient bacterium with a donor bacterium according to the first-mentioned embodiment above, and isolating the resultant transconjugant bacterium which has been modified by the inclusion of the viscosity-increasing DNA.

Another preferred embodiment of the invention relates to an improvement to a process for making multiple batches of thickneed fermented dairy product. This method includes the step of conducting the fermentation step of sequential batches using several strains of bacteria each having different phage resistance and each having thickening characteristics which correspond to those of *L. lactis* subsp. *lactis* TC67.

Still another preferred embodiment relates to an improvement to a process for producing buttermilk or sour cream by a fermentation including a bacterium capable of fermenting citrate. The improved process includes the step of conducting the fermentation also with a lactic acid bacterium harboring a first DNA fragment from a plasmid 30 MDa in molecular weight referred to as pHV67 in *L. lactis* subsp. *lactis* TC67, the DNA fragment encoding for a substance which increases viscosity of a milk-containing product, to thereby obtain buttermilk or sour cream.

Another preferred embodiment of the invention relates to an innoculum for increasing viscosity of a milk product, comprising a culture including several strains of *L. lactis* subsp. *lactis* bacteria with each strain having a different phage resistance, and a suitable carrier to maintain the viability of the culture.

Still other preferred embodiments relate to improved cottage cheese, sour cream and buttermilk and to methods of their production.

One object of this invention is to provide improved high viscosity bacteria for cultured milk products, compositions including such bacteria, and methods of the production and use of such bacteria.

Another object of this invention is to provide bacteria, methods and compositions enabling improved control of milk product fermentations.

Additional objects and advantage of the invention will become apparent upon reviewing the following description and appended claims.

DESCRIPTION OF THE PREFERRED EMBODIMENTS

For the purposes of promoting an understanding of the principles of the invention, reference will now be made to certain embodiments of the invention and specific language will be used to describe the same. It will nevertheless be understood that no limitation of the scope of the invention is thereby intended, such alterations and further modifications and applications of the principles of the invention being contemplated as would normally occur to one skilled in the art to which the invention relates.

As discussed above, certain preferred embodiments of the invention relate to a novel donor bacterium and novel compositions and methods. The novel donor bacterium harbors a first DNA fragment from a plasmid 30 MDa in molecular weight and referred to as pHV67 in *L. lactis* subsp. *lactis* TC67, the DNA fragment encoding for a substance which increases viscosity of a milk-containing product. This donor bacterium is capable of conjugally transferring the DNA fragment, for instance on a plasmid, to a lactic acid bacterium at a frequency of at least about $10^{-5}$ transconjugants per input donor bacterium. Bacterium strain TC67 has been deposited with the Agricultural Research Service Culture Collection (NRRL) under accession number NRRL-B-18702.

As further described in Example 1 below, the applicants isolated a highly viscous bacterium from a Finnish sour milk product and designated the bacterium *Lactococcus lactis* subsp. *cremoris* TF67. This strain ferments lactose (Lac+) and produces very high viscosity (Hvs+) when grown in milk. As an example, a Zahn cup #5 viscosity reading of greater than 1725 centipoise has been obtained after 100 manual shakes in a 1 l container in the applicant's work by incubating commercially available milk between 8.7 and 9.0 solids non fat and 0.5% fat containing *Lactococcus cremoris* TF67 for 16 hours at 24° C. The applicant's experimentation has demonstrated that the Hvs+phenotype of *L. cremoris* TF67 is associated with a plasmid with a molecular weight of 30 MDa, as further discussed in Example 2. This 30 MDa plasmid has been designated pHV67. By further study, it has been determined that pHV67 encodes much higher viscosity than the 18.5 MDa plasmid pSRQ2202 described by Vedamuthu and Neville, supra (see Example 4 below). Whereas pSRQ2202 produced a viscosity of 990 centipoise in a milk (8.7-9.0 solids non fat, 0.5% fat) fermentation (*L. cremoris* SCH-2, 24° C., 16h), a similar fermentation performed with *L. cremoris* TF67 conferred a viscosity of greater than 1725 centipoise.

As described in more detail in Example 3 below, conjugal transfer of pHV67 (Hvs+) was achieved in mating experiments in which *L. cremoris* TF67 was the donor and *L. lactis* LM2301 (plasmid free, Lac−, Hvs−, Phr−, Sm$^r$) the recipient. *L. lactis* LM2301 is available from Professor Todd Klaenhammer at the Department of Food Science, North Carolina State University. The resulting novel construct, designated *L. lactis* subsp. *lactis* TV67, carries both plasmid pHV67 (Hvs+) and a 65 MDa plasmid designated pLV67 (Lac+ Phr+) (see Example 2). *L. lactis* TV67 provides many advantages over *L. cremoris* TF67, including for instance not only its significantly higher donor frequency, but also higher salt (NaCl) (up to 4%) and acidity tolerance, more active growth characteristics (faster and more cells/unit volume of medium), and growth at a higher temperature range (35° to 40° C.). In addition, *L. lactis* strains are in general less vulnerable to phage than *L. cremoris* strains.

*L. lactis* TV67, which has the same thickening characteristics as *L. cremoris* TF67, serves as a high frequency conjugal donor of plasmids pHV67 and pLV67 (see for instance Example 4 below). This type of transfer is essential in strategies to transfer Hvs+ to other recipient strains using food safe selection markers such as (Lac+ Phr+) as presently required in the United States and Europe, and could not be achieved using the parent strain *L. cremoris* TF67. For instance, Example 4 describes experiments in which TV67 was used to create another high frequency donor, *L. lactis* TC67 (also having the same thickening characteristics as *L. cremoris* TF67), which was then mated with *L. lactis* strains P21, 221, and ML8, *L. cremoris* strain S26, and *L. diacetylactis* strain 806, to form P21-1, 222-1, ML8-1, S26-1 and 806-1, respectively (all Lac+ Phr+ Hvs+), which are highly effective lactic bacteria for fermentations and are further features of the invention. Strains P21-1, 222-1, ML8-1 and S26-1 have all been deposited with the Agricultural Research Service Culture Collection (NRRL) under accession numbers NRRL-B-18706 respectively. Strain 806-1 has been deposited with the Agricultural Research Service Culture Collection (NRRL) under accession numbers NRRL-B-18707 and NRRL-B-18707N.

Additionally, conjugal transfer of pHV67 from *L. lactis* TC67 or other high frequency donor constructs to other lactic bacteria, and intergeneric transfer to *S. thermophilius* and *L. bulgaricus*, opens up additional applications in the production of buttermilk, sour cream, cottage cheese dressing, cottage cheese curd, low-carlorie salad dressing, and pudding and yogurt. Moreover, the ability of the viscous bacteria of the invention to produce more viscosity per unit cell lowers the number of cells needed in a concentrate (e.g. an innoculum) to provide the desired level of functionality.

In further preferred aspects of the invention, the donor bacterium of this embodiment is able to conjugally transfer the Hvs+ DNA fragment at a frequency of at least about $10^{-4}$, and more preferably at least about $10^{-3}$ transconjugants per input donor cell. Additionally, it is preferred that the donor also harbor plasmid DNA encoding for lactose metabolism (Lac+) and be capable of conjugally cotransferring the Hvs+ and Lac+ plasmid DNA's, for instance by cotransfer of plasmids pHV67 and pLV67. Further, the novel donor bacteria can be used in methods for making highly viscous lactic acid bacteria, and these lactic acid bacteria can be used in improved methods and compositions for milk fermentations. For instance, these include inoculums which are blends of lactic acid bacteria having the Hvs+ DNA fragment such as on a plasmid but having differing phage resistance (for example, $L.$ $lactis$ strains P21-1, ML8-1 and 222-1 have phage resistances different from each other). Also included are novel methods for making lactic acid bacteria which involve the use of the donor bacterium described above, as well as novel methods for making buttermilk, sour cream, and cottage cheese which involve the use of lactic acid bacteria harboring the Hvs+ DNA fragment.

For the purpose of promoting a further understanding of the principals and advantages of the invention, the following Examples are provided.

EXAMPLE 1

Isolation of *Lactococcus lactis* subsp. *cremoris* TF67

Samples of fermented dairy products from Finland were diluted and plated on lactose indicator agar (McKay et al., 1972) for detection of strains which ferment lactose (Lac+). Lac+ colonies were evaluated for the viscous phenotype by picking them with a toothpick. A Lac+ *L. cremoris* strain, TF67, was isolated which produced viscous milk. The viscosity produced by a 1% innoculum in commercial milk (8.7–9.0% solids not fat and 0.5% fat) incubated 16 hours at 24° C. was compared between this strain and other viscous strains previously identified. Of all strains evaluated using a #5 Zahn cup Model No. 27134-005 (Boekel Industries, Philadelphia, PA) viscosity test, *L. cremoris* TF67 produced the highest viscosity.

EXAMPLE 2

Association of High Viscosity to the 30 MDa Plasmid pHV67 and Lactose Metabolism and Phage Resistance to the 65 MDa Plasmid pLV67

To evaluate whether the high viscosity phenotype (Hvs+) exhibited by *L. cremoris* TF67 (Lac+ Hvs+) was encoded by plasmid DNA, DNA curing experiments were conducted. The parental strain TF67 was found to carry seven plasmids of molecular weights 65, 35, 30, 5.5, 4.0, 3.0, and 2.2 MDa. Upon treatment of *L. cremoris* TF67 with Novobiocin (0.5 ug/ml) (Sigma Chemical Co., St. Louis, Mo.), a plasmid curing agent, Lac+ Hvs− derivatives were isolated on lactose indicator agar. Analyses comparing plasmids isolated from several Lac+ Hvs− derivatives to *L. cremoris* TF67 revealed that only the 30 MDa plasmid was absent from Lac+ Hvs− derivatives. These experiments provided indirect evidence that the 30 MDa plasmid encoded the Hvs+ phenotype.

Direct evidence for linkage of the 30 MDa plasmid to the Hvs+ phenotype and the 65 MDa plasmid to the Lac+ and phage resistance (Phr+) phenotypes was obtained using conjugation experiments. *L. cremoris* TF67 (Lac+ Hvs+) was mated with *L. lactis* LM2301 (Lac−; Hvs−; plasmid-free; streptomycin resistant, Sm$^r$) using the conjugation protocol described by McKay et al., *Appl. Environ. Microbiol.* 47:68–74 (1980), with modifications described in Example 2. Lac+ Sm$^r$ transconjugants were recovered on lactose indicator agar containing 1000 ug/ml streptomycin at a frequency of $1.7 \times 10^{-7}$ Lac+ transconjugants per input donor cell. Only Lac+ transconjugants which produced viscosity (Hvs+) or did not produce viscosity (Hvs−) were examined further.

Plasmid analyses indicated that Lac+ Hvs− transconjugants harbored only a 65 MDa plasmid designated pLV67. Lac− derivatives isolated from Lac+ Hvs− or Lac+ Hvs+ transconjugants lost only pLV67. These data confirm that conjugal transfer of the Lac+ from *L. cremoris* TF67 to *L. lactis* LM2301 correlated with transfer of pLV67. Therefore, direct evidence was provided for linkage of the Lac+ phenotype to the 65 MDa plasmid pLV67. In comparison, Lac+ Hvs+ transconjugants carried not only the 65 MDa plasmid pLV67 but a 30 MDa plasmid (designated pHV67). This indicated that pHV67 was cotransferred with pLV67 during the mating and that pHV67 was associated with the additional Hvs+ phenotype. This was confirmed by plasmid curing experiments which showed that Lac+ Hvs− derivatives of Lac+ Hvs− transconjugants lost the 30 MDa plasmid, pHV67. These data provided direct evidence which linked the Hvs+ phenotype to pHV67.

Of further interest, both Lac+ Hvs− and Lac+ Hvs+ transconjugants exhibited full resistance to small isometric phage p2 and partial resistance to prolate phage c2. This type of phage resistance is similar to abortive infection, Sing, W. D. et al. *Appl. Environ. Microbiol.* 51, 1264 (1986), which has been recognized as the most effective mechanism of defense against lactococcal phage. Lac+ Hvs− derivatives of Lac+ Hvs+ transconjugants, which carried pLV67 but not pHV67, retained similar degrees of resistance to both phages. However, Lac− derivatives of both Lac+ Hvs− and Lac+ Hvs+ derivatives (with or without pHV67) lost resistance to phage. These data indicate that the 65 MDa plasmid pLV67 carries the determinants for phage resistance (Phr+) besides those already established for Lac+. Both of these phenotypes are essential in food-grade strategies using conjugation in the lactococcal.

EXAMPLE 3

Conjugal Transfer of the High Viscosity Phenotype (Hvs+)

Conjugation was used to transfer the viscosity plasmid pHV67 (Hvs+) from *L. cremoris* TF67 to *L. lactis* LM2301 (plasmid-free, Lac−, Hvs−, Sm$^r$). Agar-surface matings (conjugation) were conducted as described previously by McKay et al. (1980), supra, with the following modifications. Lac+ and Hvs+ conjugal transfer was obtained by using *L. cremoris* TF67 cells grown in M17 broth for 5 hours at 30° C., resuspending them in fresh M17 broth, an adjusting the cell concentration to an optical density of 0.25–0.5 before combining with *L. lactis* LM2301 recipients. The ratio of *L. cremoris* TF67 donor cells to *L. lactis* LM2301 recipient cells used was 1:3. The donor/recipient cell mixture was washed twice in M17 broth. A volume of 200 ul of donor/recipient cell mixture was plated on M17 agar supplemented with 0.5% glucose and incubated 16 hours at 30° C. Conjugation mixtures were recovered using M17 broth, diluted in streptomycin. Lac+ colonies were enumerated after incubation for 48 h at 30° C. for Lac+ transfer frequency and evaluated for viscosity (Hvs+) by picking with a toothpick. The frequency of Lac+ transfer was low ($1.7 \times 10^{-7}$ Lac+ transconjugants/input donor cell). However, approximately 95% of the Lac+ transconjugants were Hvs+ suggesting a high probability of Lac+ and Hvs+ transfer due to pLV67 and pHV67 cotransfer. Lac+ Hvs+ transconjugants were purified on lactose indicator agar and tested for lactococcal species (*L. lactis* or *L. cremoris*) based on deamination of arginine in Reddy's differential broth. Plasmid analyses were also conducted on Lac+ Hvs+ *L. lactis* transconjugants to differentiate *L. cremoris* TF67 donors from *L. lactis* LM2301 recipients. One representative Lac+ Hvs+ transconjugant was designated *L. lactis* TV67 (pLV67, Lac+ Phr+; pHV67, Hvs+; Sm$^r$).

EXAMPLE 4

Food-Grade Dissemination of Plasmids Encoding Lactose Metabolism, Phage Resistance, and High Viscosity From a High Frequency Donor to Lactic Acid Bacterial Recipients Successful transfer of plasmid encoded traits in lactococci using food-grade techniques is facilitated by high frequency conjugal transfer systems and adequate food grade selection markers such as lactose metabolism and phage resistance. Although *L. cremoris* TF67 demonstrated the ability to transfer Lac+ Phr+ and Hvs+ to *L. lactis* recipients, the transfer frequency was very low ($1.7 \times 10^{-7}$ Lac+ transconjugants/input donor cell). This condition would make transfer of Hvs+ and selection of transconjugants using food-grade markers such as lactose metabolism and phage resistance highly impracticable.

When the ability of *L. lactis* TV67 to transfer Lac+ and Hvs+ phenotypes was evaluated, the transfer frequency was found to be more than $10^4$ times higher than that of parental strain *L. cremoris* TF67, on the order of $10^{-3}$ or more transconjugants per input donor cell. Therefore, *L. lactis* TV67 serves as a high frequency donor of Lac+ and Hvs+. To create a *L. lactis* donor which did not carry antibiotic resistance traits, *L. lactis* TV67 (pLV67, Lac+ Phr+; pHV67, Hvs+) was mated with a Lac− antibiotic sensitive recipient, designated C145 (Lac−, Hvs−, plasmid-free, Sm$^s$) (also known as LM0230). Several Lac+ transconjugants were recovered on lactose indicator agar, scored for Hvs+ (viscous colony), and screened for antibiotic sensitivity by replica plating. One representative antibiotic sensitive Lac+ Hvs+ transconjugant carrying pLV67 (Lac+ Phr+) and pHV67 (Hvs+) was designated *L. lactis* TC67.

Creation of the food-grade high frequency donor *L. lactis* TC67 allowed its direct use to disseminate pLV67 (Lac+Phr+) and pHV67 (Hvs+) to other strains. Subsequently, *L. lactis* subsp. *lactis* TC67 was used in conjugal matings with Lac−Hvs−Phr− recipient strains *L. lactis* P21, 222, and ML8. Transconjugants were selected based on Lac+ and Phr+. Prolate phage c2 was used to eliminate *L. lactis* TC67 donor populations while homologous phage were used to eliminate Lac−Hvs−Phr− recipient strains.

Plasmid analyses comparing Lac+Phr+Hvs+ isolates from these matings to donor and recipient strains demonstrated that these were in fact transconjugants. All *L. lactis* transconjugants, designated P21-1, 222-1, and ML8-1, acquired pHV67 and pLV67 and produced equivalent viscosities, growth rates, and resistance to homologous phage comparable to that of *L. lactis* TV67 and *L. lactis* TC67. These strains thus provided for several separate milk fermentations with each fermentation having its own bacterial strain with each strain having a different phage resistance. Thus, a bacterial rotation and protection against phage attack was realized. Alternatively, these bacteria can be blended in an innoculum to provide insurance against phage sensitive failure of any individual strain.

Whereas only one known strain (*L. cremoris* TF67) existed before which produced very high viscosity, a multiple of different strains have been generated using pHV67 and pLV67 enabling a full strain rotation to be employed. Furthermore, where no known *L. lactis* subsp. *lactis* strains existed which produce very high viscosity, numerous different *L. lactis* subsp. *lactis* strains have been produced by applicant's invention which grow faster in M17 broth, produce more acid per unit time, and grow at a higher temperature. Where few phage resistant strains existed that produced viscosity at any level, now numerous strains exist which are phage resistant and produce high viscosity. In conjunction with traditional rotation strategies, this internal resistance encoded by pLV67 (phr−, abortive infection phage resistance mechanism) provides an additional level of protection. Accordingly, the applicant's invention finally addresses the need and demand for new fermentation systems enabling high levels of reliability and control as well as other advantages.

EXAMPLE 5

Fermentations Demonstrating Increased Endproduct Viscosity

The growth of Hvs+ *L. lactis* transconjugants was compared to commercial viscous *L. cremoris* strains in milk. A 1% innoculum of each strain was added to commercial milk (8.7-9.0% solids not fat and 0.5% fat) and incubated for 16 h at 24° C. Colony forming units per ml (CFU/ml) were enumerated and viscosity of milk evaluated at each hour interval. Hvs+ *l. lactis* P21-1, 222-1, and ML8-1 transconjugants grew at a faster rate, produced more viscosity per unit time, and achieved higher final cell counts than the native Finnish strain *L. cremoris* TF67 or viscous lactococci strains presently used in the industry (including *L. cremoris* and *lactis* strains carrying pSRQ2202). Therefore, the Hvs+ *L. lactis* transconjugants have the potential to produce more viscosity in milk than any strains identified thus far from commercial sources.

In other experiments which evaluated the maximum growth temperatures of Hvs+ *L. lactis* transconjugants and viscous *L. cremoris* strains, it was found that the Hvs+ *L. lactis* transconjugants grew at a higher temperature (35° C.-40° C.) whereas *L. cremoris* strains did not grow significantly. Therefore, the Hvs+ *L. lactis* transconjugants are applicable in higher temperature fermentation which may decrease fermentation times for conventional culture processes or in thermophillic fermentations such as production of yogurt, Swiss cheese, and Italian cheese.

The application of newly created Hvs+ *L. lactis* transconjugants to improve viscous dairy products provides a useful alternative to existing approaches. Hvs+ *L. lactis* strains grow faster and heartier than the currently used viscous lactococci strains do. Since the new Hvs+

L. lactis strains produce a greater viscosity per cell, a lower proportion of these strains is used effectively to achieve a higher viscosity endproduct without offsetting the balance with non-viscous lactococci strains. When used in culture with predominating lactococci non-viscous strains, they maintain balanced growth due to their similar growth characteristics. In this way, shorter fermentation times are maintained using a culture in which all strains grow fast. Also, better growth of L. lactis strains with commercial non-viscous strains allows production of a very high viscosity endproduct. In turn, this high viscosity endproduct is able to withstand longer periods of storage before reaching a minimal viscosity. Furthermore, by constructing L. lactis strains with internal abortive infection resistance mechanisms (pLV67, Phr+), a level of defense against phage attack is provided. By dissemination of both Phr+ and Hvs+ characteristics to other L. lactis strains to create a series of strains, each specific for different phages, a second level is provided of safe use of strains at a higher proportion with respect to non-viscous strains in fermentation which need to attain maximum viscosity. Lastly, these L. lactis strains develop enough acidity in conjunction with non-viscous lactococci to enhance the flavor of the viscous product.

EXAMPLE 6

Fermentations with Balanced Growth Between Lac+Hvs+ L. lactis Strains and Non-viscous Lactococcal Strains Another feature of the invention provides construction of paired strains with matched growth rates. Since independent phenotypes are encoded on separate plasmids pHV67 (Hvs+) and pLV67 (lac$^{30}$ Phr+), the flexibility exists to create both Lac+ Hvs− and Lac+ Hvs+ transconjugants from the same lactococcal strain. These created strains have matched growth rates based on identical genetic backgrounds except for the Hvs+ plasmid pHV67. In this way, endproduct viscosity is fine tuned based on different proportions of the Lac+ Hvs+ and Lac+Hvs− strains without regard to variations in the growth rates of the bacteria caused by physical and biological effects. Endproduct viscosity can thus be predictably forecast since there is more precise balance between strains. Both viscous and non-viscous derivatives react similarly to changes in temperature, pH, and availability of nutrients, physical processing parameters which often change endproduct viscosity.

EXAMPLE 7

Methods for Making Buttermilk and Sour Cream

Conventional fermentations to make buttermilk and sour cream are conducted. These fermentations include the use of bacteria which can ferment citrate, as well known in the industry. However, in addition, the fermentation is conducted with L. lactis P21-1. P21-1 provides superior thickening and smooth texture in the fermentations, and very satisfactory sour cream and buttermilk are thereby produced. Similar successful buttermilk and sour cream fermentations are achieved using L. cremoris S26-1 instead of L. lactis P21-1.

EXAMPLE 8

Method for Making Cottage Cheese

L. diacetylactis 806-1 is used in a conventional process for making cottage cheese (see U.S. Pat. No. 3,968,256 issued to Sing, 1976, which is hereby incorporated by reference in its entirety). The resulting cheese product have improved texture, demonstrating advantages provided by using this novel bacterium.

While the invention has been illustrated and described in detail in the foregoing description, the same is to be considered as illustrative and not restrictive in character, it being understood that only the preferred embodiments have been described and that all changes and modifications that come within the spirit of the invention are desired to be protected.

What is claimed is:

1. In a process for making a thickened fermented dairy product, which process comprises a step whereby a liquid dairy product is fermented by bacteria, the improvement which comprises conducting the fermentation step using two or more genetically distinct strains of bacteria which harbor a first DNA fragment from a plasmid 30 MDa in molecular weight and referred to as pHV67 in L. lactis subsp. lactis TC67, said DNA fragment encoding for a substance which increases the viscosity of a fermented dairy product.

2. In a process for producing buttermilk or sour cream by fermentation of a liquid dairy product by a lactic acid bacterium, the improvement wherein the fermentation process utilizes a lactic acid bacterium harboring a first DNA fragment from a plasmid 30 MDa in molecular weight and referred to as pHV67 in L. lactis subsp. lactis TC67, said DNA fragment encoding for a substance which increases viscosity of a milk-containing product, to thereby obtain buttermilk or sour cream.

3. A process according to claim 2, wherein said lactic acid bacterium is a *Lactococcus lactis* subsp. *lactis* strain.

4. A process according to claim 2, wherein said lactic acid bacteria is a *Lactococcus lactis* subsp. *cremoris* strain.

5. A process according to claim 2, which is a process for producing buttermilk.

6. A process according to claim 2, which is a process for producing sour cream.

7. In buttermilk, comprising a cultured sour milk made by the bacterial fermentation of milk, the improvement comprising the inclusion of a lactic acid bacterium harboring a first DNA fragment from a plasmid 30 MDa in molecular weight and referred to as pHV67 in L. lactis subsp. lactis TC67, said DNA fragment encoding for a substance which increases viscosity of a milk-containing product.

8. A product according to claim 7, wherein said lactic acid bacterium is a *Lactococcus lactis* subsp. *lactis* strain.

9. A product according to claim 7, wherein said lactic acid bacteria is a *Lactococcus lactis* subsp. *cremoris* strain.

10. In sour cream, comprising cream which has been soured by bacterial fermentation, the improvement comprising the inclusion of a lactic acid bacterium harboring a first DNA fragment from a plasmid 30 MDa in molecular weight and referred to as pHV67 in L. lactis subsp. lactis TC67, said DNA fragment encoding for a substance which increases viscosity of a milk-containing product.

11. A product according to claim 10, wherein said lactic acid bacterium is a *Lactococcus lactis* subsp. *lactis* strain.

12. A product to claim 10, wherein said lactic acid bacteria is a *Lactococcus lactis* subsp. *cremoris* strain.

13. In cottage cheese, comprising a soft, white cheese made of curds of skim milk, the improvement comprising the inclusion of a lactic acid bacterium harboring a first DNA fragment from a plasmid 30 MDa in molecular weight and referred to as pHV67 in *L. lactis* subsp. *lactis* TC67, said DNA fragment encoding for a substance which increases viscosity of a milk-containing product.

14. A product according to claim 13, wherein said lactic acid bacterium is a *Lactococcus lactis* subsp. *diacetylactis* strain.

15. A process according to claim 1, wherein all strains used in the fermentation process harbor a first DNA fragment from a plasmid 30 MDa in molecular weight and referred to as pHV67 in *L. lactis* subsp. *lactis* TC67, said DNA fragment encoding for a substance which increases the viscosity of a fermented dairy product.

16. A process according to claim 1, wherein strains harboring a first DNA fragment from a plasmid 30 MDa in molecular weight and referred to as pHV67 in *L. lactis* subsp. *lactis* TC67, said DNA fragment encoding for a substance which increases the viscosity of a fermented dairy product, and strains which do not harbor said first DNA fragment are used together in fermentation.

17. A process according to claim 1, wherein high viscosity and no viscosity strains are used together in fermentation.

18. In a process for making a thickened fermented dairy product, which process comprises a step whereby a liquid dairy product is fermented by bacteria, the improvement which comprises conducting the fermentation step using bacteria which harbor a first DNA fragment from a plasmid 30 MDa in molecular weight and referred to as pHV67 in *L. lactis* subsp. *lactis* TC67, said DNA fragment encoding for a substance which increases the viscosity of a fermented dairy product, but which are not concentrated by centrifugation in the manufacture of culture used for the fermentation.

19. A process according to claim 1, wherein said strains are concentrated using centrifugation in the manufacture of culture used for the fermentation.

20. A process according to claim 1, wherein said genetically distinct strains of bacteria are each susceptible to different bacteriophage strains, and are used randomly as single strain starter cultures in fermentation.

21. A process according to claim 1, wherein said genetically distinct strains of bacteria are each susceptible to different bacteriophage strains, and are used simultaneously as a blend of separate single strain starter cultures for fermentation.

22. A process according to claim 1, wherein said genetically distinct strains of bacteria are each susceptible to different bacteriophage strains, and are combined and used as a multiple strain starter culture for fermentation.

23. A process according to claim 1, wherein said genetically distinct strains of bacteria are each susceptible to different bacteriophage strains, and are used as single strain starter cultures in rotation for sequential batches of fermentation.

24. A process according to claim 1, wherein said genetically distinct strains of bacteria are each susceptible to different bacteriophage strains, and are combined and used as multiple strain starter cultures in rotation for sequential batches of fermentation.

25. A process according to claim 1, wherein said genetically distinct strains of bacteria are phage resistant and are used in rotation for sequential batches of fermentation.

26. A process according to claim 1, wherein said genetically distinct strains of bacteria are phage resistant and are used singley in fermentation.

27. A process according to claim 1, wherein said genetically distinct strains of bacteria are phage resistant and are combined to compose a multiple strain starter culture and used in fermentation.

28. A process according to claim 1, wherein individual, phage resistant strains of said genetically distinct strains of bacteria are combined to compose a multiple strain starter culture and used in rotation for sequential batches of fermentation.

29. A process according to claim 1, wherein said genetically distinct strains of bacteria grow at temperatures between 20° C. and 40° C. and exhibit stable production of viscosity.

30. A process according to claim 1, wherein said genetically distinct strains of bacteria grow at temperatures between 20° C. and 40° C. and exhibit stable resistance to bacteriophage.

31. A process according to claim 1, wherein said genetically distinct strains of bacteria grow at temperatures between 20° C. and 40° C. and exhibit stable lactose metabolism.

32. A method according to claim 1, wherein said strains are of the species *L. lactis* subsp. *lactis*.

33. A method according to claim 1, wherein said strains are of the species *L. lactis* subsp. *cremoris*.

34. A method according to claim 32, wherein said strains include *L. lactis* subsp. *lactis* P21-1, ML8-1 or S26-1.

35. In a process for making a thickened fermented dairy product, which process comprises a step whereby a liquid dairy product is fermented by bacteria, the improvement which comprises conducting the fermentation step using two or more bacteria from the same recipient or parent strain, at least one of said bacteria harboring a first DNA fragment from a plasmid 30 MDa in molecular weight and referred to as pHV67 in *L. lactis* subsp. *lactis* TC67, and at least one of said bacteria not harboring said first DNA fragment.

* * * * *